United States Patent [19]

Fake

[11] 4,011,329
[45] * Mar. 8, 1977

[54] TETRAHYDROPYRID-4-YL-CHROMAN-5-OL DERIVATIVES IN THE TREATMENT OF HYPERTENSION

[75] Inventor: Charles Sylvester Fake, Harlow, England

[73] Assignee: Beecham Group Limited, England

[ * ] Notice: The portion of the term of this patent subsequent to Aug. 3, 1993, has been disclaimed.

[22] Filed: Aug. 20, 1975

[21] Appl. No.: 606,251

Related U.S. Application Data

[60] Division of Ser. No. 504,087, Sept. 9, 1974, Pat. No. 3,960,880, which is a continuation-in-part of Ser. No. 324,222, Jan. 16, 1973, Pat. No. 3,853,899.

[30] Foreign Application Priority Data

Jan. 26, 1972 United Kingdom ............... 3654/72

[52] U.S. Cl. .......................... 424/263; 424/248.58; 424/267; 424/274
[51] Int. Cl.² ................. A61K 31/40; A61K 31/44; A61K 31/445; A61K 31/535
[58] Field of Search .................... 424/248, 263, 267

*Primary Examiner*—Stanley J. Friedman

[57] ABSTRACT

Compounds of the formula:

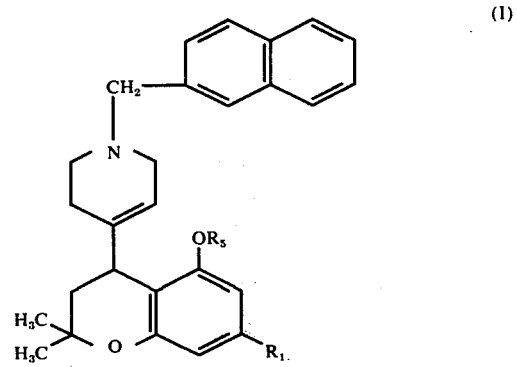

and their pharmaceutically acceptable non-toxic salts, wherein $R_1$ is alkyl of 5 to 8 carbon atoms which is straight chained or α-substituted by a methyl group or α,α-disubstituted by methyl groups and $R_5$ is hydrogen, $R_6$ or $CO.R_6$ wherein $R_6$ is alkyl of 1 to 4 carbon atoms or alkyl of 1 to 4 carbon atoms substituted by $NR_7R_8$ wherein $R_7$ and $R_8$ are each hydrogen or alkyl of 1 to 4 carbon atoms or $NR_7R_8$ is pyrrolidino, piperidino or morpholino, have been found to possess good antihypertensive activity while being of low-toxicity and substantially free of sedative side effects.

32 Claims, No Drawings

TETRAHYDROPYRID-4-YL-CHROMAN-5-OL DERIVATIVES IN THE TREATMENT OF HYPERTENSION

This is a division of Ser. No. 504,087 filed Sept. 9, 1974, now U.S. Pat. No. 3,960,880, which, in turn, is a continuation-in-part of Ser. No. 324,222 filed Jan. 16, 1973 and which issued on Dec. 10, 1974, as U.S. Pat. No. 3,853,899.

The present invention is concerned with compounds of the formula

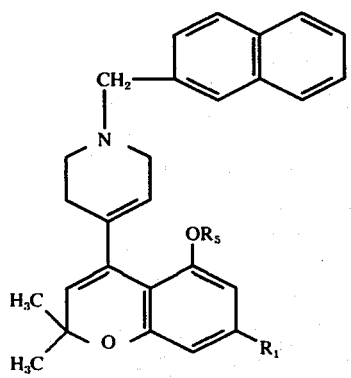

(I)

and their pharmaceutically acceptable non-toxic salts, wherein $R_1$ is alkyl of 5 to 8 carbon atoms which is straight chained or α-substituted by a methyl or α, α-disubstituted by methyl groups and $R_5$ is hydrogen, $R_6$ or $CO.R_6$ wherein $R_6$ is alkyl of 1 to 4 carbon atoms or alkyl of 1 to 4 carbon atoms substituted by $NR_7R_8$ wherein $R_7$ and $R_8$ are each hydrogen or alkyl of 1 to 4 carbon atoms or $NR_7R_8$ is pyrrolidino, piperidino or morpholino.

These compounds are useful for their anti-hypertensive activity. They possess low-toxicity and are substantially free of sedative side effects.

BACKGROUND TO THE INVENTION

British Pat. No. 1,360,009 discloses, inter alia, compounds of the formula (II):

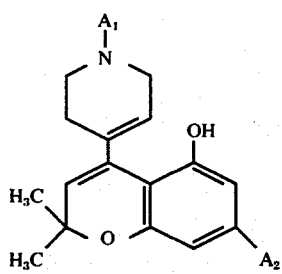

(II)

and their salts, esters and ethers wherein $A_1$ is a hydrocarbon group of 1 – 20 carbon atoms and $A_2$ is an alkyl group of 1 – 20 carbons. Such compounds are now known to possess anti-hypertensive activity of a good level. However, a detailed study has shown that the compounds disclosed in that application have a level of renal toxicity which, while not being of such a level as to necessarily rule out the use of the compounds of formula (I) as short term anti-hypertensives, is sufficiently high to suggest that the compounds of formula (I) are not suitable for long term therapy.

A considerable advance was reached with the development of the compounds specifically described in United States Application Ser. No. 324222. The preferred compounds of that application were those of the formula (III):

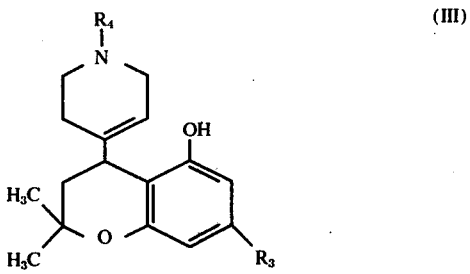

(III)

and their salts, wherein $R_3$ is alkyl of 4 to 10 carbon atoms and $R_4$ is a hydrocarbon of 7 to 12 carbon atoms preferably 2-propenyl, 2-phenylethyl, benzyl, 1-naphthylmethyl or 2-naphthylmethyl. It was found that these compounds had a high level of anti-hypertensive activity coupled with low central nervous system depressant activity and improved renal toxicity.

It has now been surprisingly discovered that a particularly good level of anti-hypertensive activity coupled with a particularly low level of central nervous system depressant activity and a greatly reduced level of renal toxicity is exhibited by a particularly sub-group of those compounds.

At present no explanation for the improved properties can be given but repeated tests have confirmed them.

DESCRIPTION OF THE INVENTION

The present invention thus provides compounds of the formula (I):

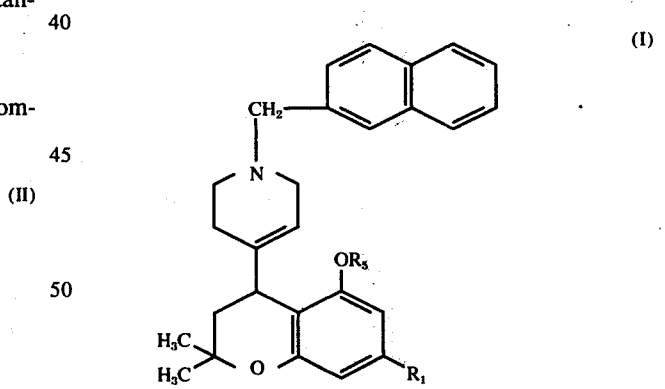

(I)

and their pharmaceutically acceptable non-toxic salts, wherein $R_1$ is alkyl of 5 to 8 carbon atoms which is straight chained or α-substituted by a methyl group or α, α-disubstituted by methyl groups and $R_5$ is hydrogen, $R_6$ or $CO.R_6$ wherein $R_6$ is alkyl of 1 to 4 carbon atoms or alkyl of 1 to 4 carbon atoms substituted by $NR_7R_8$ wherein $R_7$ and $R_8$ are each hydrogen or alkyl of 1 to 4 carbon atoms or $NR_7R_8$ is pyrrolidino, piperidino or morpholino.

If desired the compounds of formula (I) may be in the form of a hydrate, e.g. the monohydrate.

A particularly preferred group of compounds of the present invention are those compounds of formula (I)

wherein $R_5$ is hydrogen and $R_1$ is alkyl of 5 or 6 carbon atoms.

Another preferred group of compounds of formula (I) are those of formula (IV):

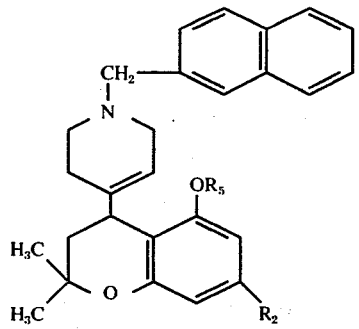

(IV)

and pharmaceutically acceptable non-toxic salts thereof wherein $R_2$ is n-amyl, n-hexyl or 2-hexyl and $R_5$ is hydrogen, $R_6$ or $CO.R_6$ wherein $R_6$ is alkyl of 1 to 4 carbon atoms.

Preferably $R_2$ is n-amyl.

Suitable salts of the present invention include non-toxic acid addition salts formed with inorganic or organic acids such as hydrochloric, hydrobromic, phosphoric, sulphuric, methanesulphonic, toluenesulphonic, acetic, propionic, citric, lactic, tartaric, succinic, mandelic, glutamic, glucuronic or like acid.

Ethers and esters of the present invention include those of the formula (V):

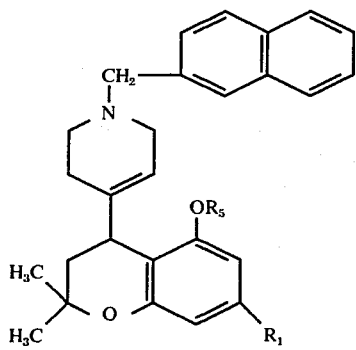

(V)

wherein $R_1$ is as above defined and $R_5$ is $R_6$ or $CO.R_6$ wherein $R_6$ is alkyl group of 1 to 4 carbon atoms or alkyl of 1 to 4 carbon atoms substituted by $NR_7R_8$ wherein $R_7$ is hydrogen or alkyl of 1 to 4 carbon atoms, $R_8$ is hydrogen or alkyl of 1 to 4 carbon atoms or $NR_7R_8$ is a pyrrolidino, piperidino or morpholino ring.

Most suitably, $R_6$ is methyl, ethyl or propyl optionally substituted by dimethylamino, diethylamino, pyrrolidyl or piperidyl.

Preferably $R_6$ is methyl.

A further preferred group of compounds of this invention are of the formula:

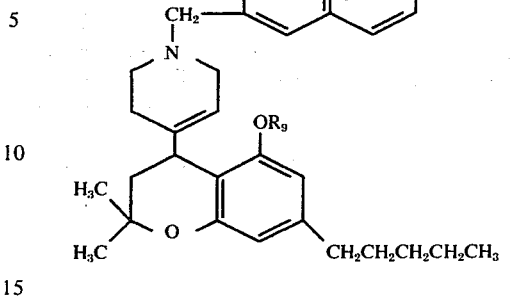

(VI)

and pharmaceutically acceptable non-toxic salts thereof wherein $R_9$ is hydrogen, methyl or acetyl.

The compound of formula (IV) wherein $R_9$ is hydrogen combines a particularly high level of anti-hypertensive activity with a particularly low level of disadvantageous features such as sedation or renal toxicity.

The compounds of formula (I) may be prepared by the reduction of a compound of the formula (VII):

(VII)

wherein $R_1$ is as above defined, $R_5$ is hydrogen and B is an anion such as Cl, Br, I or the like.

The ethers of the compounds of formula (I) ($R_5$ is $R_6$), may be prepared by the reduction of the corresponding ether of the compounds of formula (VII).

The esters and ethers of the compounds of formula (I) ($R_5$ is $R_6$ or $CO.R_6$) may be prepared from the corresponding compound of formula (I) wherein $R_5$ is hydrogen, or an alkali metal salt thereof by conventional methods of alkylation or acylation such as reaction with a compound of the formula $Cl.R_6$ or $Cl.CO.R_6$ or the like. If $R_6$ contains a basic group, the compound may be used in the form of its acid addition salt if desired.

The reduction of the compound of formula (VII) wherein $R_5$ is hydrogen, may be brought about by catalytic hydrogenation or by reaction with a complex hydride such as a borohydride, for example, sodium borohydride.

Reduction with sodium borohydride is a particularly useful method of preparing the above compounds.

Such a reaction may take place at any non-extreme temperature. As is expected in organic chemistry, the lower the temperature used, the longer the period for reaction. It has been found that a suitable temperature range for carrying out the reaction is between 0° C and 100° C for example, 5° C to 80° C. It is often very convenient to carry out the reaction at ambient temperature.

The reduction reaction will normally take place in an organic solvent in conventional fashion. If sodium borohydride is used suitable solvents include lower alkanols or mixtures of a lower alkanol and water. Aqueous ethanol and aqueous methanol are particularly convenient solvents for this reaction.

Certain of the reaction products or starting materials may be subject to aerial oxidation in solution. Consequently it is often advantageous to prepare and isolate the compounds of this invention under an inert atmosphere, for example, under nitrogen.

If the compound of formula (I) required is a hydrate, this may often be accomplished by the simple expedient of recrystallising the anhydrous material from aqueous methanol. Once formed such hydrates are generally stable, for example, on melting they frequently solidify (on cooling) as the hydrate and not as the anhydrous form as might have been expected.

The useful intermediates of formula (VII) are novel and may be prepared by the reaction of a compound of the formula (VIII):

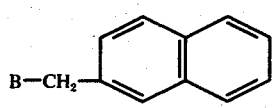

(VIII)

wherein B is Cl, Br or I, with a compound of the formula (IX):

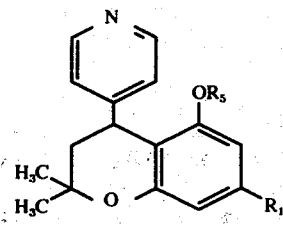

(IX)

wherein $R_1$ is as above defined and $R_5$ is hydrogen.

The quaternization of the pyridyl derivative of formula (IX) may take place under conventional conditions such as those described in Ser. No. 324222. Such nucleophilic displacement reactions take place in conventional solvents such as acetone, ether, dimethylformamide or the like at low, ambient or elevated temperatures. Generally, elevated temperatures are used, e.g. at the reflux point of the solvent.

The ethers of the compounds of formula (VII) ($R_5$ is $R_6$) may be prepared by reacting a sodium salt of the compound of the formula (IX) with an alkylhalide in conventional manner.

The compounds of formula (IX) may be prepared by the general techniques described in the published specification of German Application No. 2,253,900.

When tested on several species of mammals the compounds of this invention have been found to depress blood pressure in hypertensive animals. The present invention, therefore includes pharmaceutical compositions comprising an anti-hypertensive amount of a compound of formula (I) or a pharmaceutically acceptable non-toxic salt thereof or hydrate thereof in combination with a pharmaceutically acceptable non-toxic inert diluent or carrier.

The compositions of the invention may be administered orally or parenterally. Typical oral formulations include pills, tablets, capsules, sachets, granules, powders, chewing-gums, suspensions, emulsions and solutions, particularly suitable oral formulations are tablets and capsules and like shaped-forms. Where appropriate and where necessary in accordance with the practice of the pharmaceutical arts, the formulations may include diluents, binding agents, dispersing agents, lubricating agents, coating materials, buffering agents, flavouring agents, colouring agents, solvents, thickening agents, suspending agents, sweeteners or any other pharmaceutically acceptable additions, for example, gelatin, mannitol, lactose, starch, talc, magnesium stearate, stearic acid, hydrogenated oils, polyglycols and syrups in agreement with conventional practice. Where the formulations are tablets or capsules and the like, they will represent pre-measured unit dose but in the case of granules, powders, suspensions and the like, the formulations may be presented as pre-measured doses or in multi-dose containers from which the appropriate unit dose may be withdrawn.

Injectable forms are generally not preferred because of the low solubility of the compounds of formula (I) but low dosages may be administered in this manner. The injectable form is generally in aqueous solution (although non-aqueous solution may be used if required), suspension or emulsion in a pharmaceutically acceptable liquid (such as sterile pyrogen-free water or parenterally acceptable oils) or mixtures of liquids which may contain non-toxic anti-microbial agents, anti-oxidants or other preservatives, buffers (preferably in the physiological pH range of 6.5 – 7.0), solutes to render the solution isotonic with blood, thickening agents, suspending agents or other pharmaceutically acceptable additives. Such forms are normally presented in unit dose form such as ampoules or disposable injection devices or in multi-dose forms such as a bottle from which the appropriate dose may be withdrawn, or as a solid form or concentrate which can be used to quickly prepare an injectable formulation. All formulations for injection are rendered sterile.

Normally orally administrable compositions will be preferred because of their much greater case of administration.

Similarly, dosage forms containing fixed, predetermined amounts are normally preferred because of the need for accuracy in dosing.

If desired the compositions of this invention may contain further anti-hypertensive agents and/or diuretics.

A particularly suitable form of the pharmaceutical composition of this invention will comprise a solid, shaped dosage form which comprises from 0.05 mg to 1500 mg of a compound of formula (I) or pharmaceutically acceptable salt, ester or ether thereof as described hereinbefore.

Most suitable such a dosage form is a tablet, capsule or like conventional dosage forms.

Such dosage forms may be taken once, twice, three, four or more times a day so that for a 70 kg adult the daily dose administered is from 0.25 mg to 1500 mg, for example, 1 mg to 1000 mg.

Compound of formula (I) may exist in optically active forms and these are included in the invention.

The following Examples illustrate the preparation of some of the compounds of this invention and their pharmacological effects:-

EXAMPLE 1

7-(2-Hexyl)-4-[1-(2-naphthylmethyl)-1,2,5,6-tetrahydro-4-pyridyl]-2,2-dimethylchroman-5-ol 7-(2-Hexyl)-2,2-dimethyl-4-(4-pyridyl) chroman-5-ol (6.78 g) and 2-bromomethylnaphthalene (4.86 g) were dissolved in acetone (100 ml) (under $N_2$) and refluxed under $N_2$) for 23 hours. Concentration to small volume followed by addition of ether precipitated 1-(2-naphthylmethyl)-4-[7-(2-hexyl)-2,2-dimethyl-5-hydroxychroman-4-yl]pyridinium bromide (9.85 g). Recrystallisation from ethanol/diethyl ether gave pure product (7.37 g, 66%) m.p. 138°–141° C.

The quaternary salt (7.37 g) was dissolved in a mixture of ethanol (150 ml) and water (50 ml) and the solution was stirred at ambient temperature whilst an excess of sodium borohydride (1.1 g) was added portionwise over 30 minutes. The resulting suspension was stirred for a further 30 minutes at ambient temperature and water (150 ml) was added followed by ether (300 ml). The organic layer was separated, washed with water (50 ml), dried over magnesium sulphate and evaporated under reduced pressure to yield the crude product (5.91 g). This crude product was dissolved in a mixture of diethyl ether and petroleum ether (60°–80°) and purified by column chromatography on silica gel. 7-(2-Hexyl)-4-[1-(2-naphthylmethyl)-1,2,5,6-tetrahydro-4-pyridyl]-2,2-dimethylchroman-5-ol (2.18 g) was obtained as an amorphous solid, m.p. 49°–52° C.

EXAMPLE 2

7-n-Pentyl-4-[1-(2-naphthylmethyl)-1,2,5,6-tetrahydro-4-pyridyl-2,2-dimethylchroman -5-ol 7-n-Pentyl-2,2-dimethyl-4-(4-pyridyl)chroman-5-ol (24.2 g) and 2-bromomethylnaphalene (16.8 g) were dissolved in dry acetone (380 ml) and the mixture refluxed for 12.5 hours under nitrogen. The clear brown solution was left standing for 72 hours at ambient temperature (roughly 17° C) under nitrogen. At the end of this time colourless crystals of 1-(2-naphthylmethyl)-4-[7-n-pentyl-2,2-dimethyl-5-hydroxychroman-4-yl]pyridinium bromide (26.9 g) had been deposited from solution (m.p. 198°–200° C).

The quaternary salt (26.9 g) was dissolved in a mixture of ethanol (330 ml) and water (110ml) under nitrogen and sodium borohydride (3.5 g) was added portionwise to the stirred solution over 0.5 hours. At the end of the addition the suspension was stirred for a further 0.5 hour, and then diluted with ether (500 ml) and water (300 ml). The organic layer was dried over anhydrous sodium sulphate, filtered and evaporated in vacuo to yield the crude product as a yellow foam (22.3 g). This crude material was purified via column chromatography (using Kieselgel 60 and ethyl acetate) to yield 7-n-pentyl-4-[1-(2-naphthylmethyl)-1,2,5,6-tetrahydro-4-pyridyl]-2,2-dimethylchroman-5-ol as a pale yellow amorphous solid, m.p. 49°–51.5° C. [Recrystallised from 60°–80° petroleum ether to give colourless needles, m.p. 78°–80° C.].

The tetrahydropyridine (4.70 g.) and D-(+)-tartaric acid (1.50 g) were together dissolved in ethanol and the solution was evaporated to dryness under reduced pressure to yield a non-crystalline white solid m.p. 95°–115° C dec. Crystallization from ethanol/diethyl ether yielded the D-(+)-hydrogen tartrate salt as colourless microcrystals, m.p. 105°–125° C dec.

Similarly, the tetra hydropyridine (1.41 g) and citric acid (0.63 g) were dissolved together in acetone and the solution was evaporated to give the dihydrogen citrate salt as a colourless microcrystals, m.p. 75°–100° C dec (exacetone/diethyl ether).

EXAMPLE 3

7-n-Pentyl-4-[1-(2-naphthylmethyl)-1,2,5,6-tetrahydro-4-pyridyl]-2,2-dimethylchroman-5-ol monohydrate A sample of the anhydrous material produced in Example 2 was recrystallised from the minimum quantity of aqueous methanol to yield the title compound, m.p. 80–100° C approx.

EXAMPLE 4

Biology i. When tested by oral dosing on deoxycorticosterone/NaCl-treated hypertensive rats, the compound of Examples 2 and 3 produced the following results:

| Dose (mg/kg) | Example No. | No. of animals in group | No. of animals died under test | % Fall in Systolic Blood Pressure | | |
|---|---|---|---|---|---|---|
| | | | | 4 hr | 6 hr | 24 hr |
| 10 | 2 | 6 | 0 | 4 | 11 | 10 |
| | 3 | 6 | 0 | 1 | 9 | 3 |
| 30 | 2 | 6 | 0 | 12 | 16 | 10 |
| | 3 | 6 | 0 | 9 | 13 | 7 |
| 100 | 2 | 6 | 0 | 16 | 25 | 17 |
| | 3 | 6 | 0 | 14 | 25 | 6 |
| 300 | 2 | 6 | 0 | 26 | 32 | 38 |
| | 3 | 6 | 0 | 29 | 25 | 26 |
| 1000 | 2 | | Not tested | | | |
| | 3 | 3 | 0 | 25 | 21 | 29 |

All rats receiving the 1000 mg/kg dose of Example 3 had profuse diarrhoea and two of the rats receiving the 300 mg/kg dose had slight diarrhoea. No diarrhoea was observed in the rats receiving 300 mg/kg of Example 2. Also no diarrhoea was observed with Example 2 in normotensive rats at 1000 mg./kg p.o. or in mice at 900 mg/kg p.o. No definite evidence of any sedation or ptosis was observed at any of the above doses with both Examples.

In deoxycorticosterone/NaCl-treated hypertensive rats, reserpine produced falls in systolic pressure (greater than 20%) in doses of 1–10 mg/kg p.o. and α-methyldopa was effective at 100–300 mg/kg p.o. Ptosis, sedation and diarrhoea was occasionally observed with the 10 mg/kg dose of reserpine.

ii. The compound of Example 3 was administered orally at a dose level of 100 mg/kg to 2 renal hypertensive cats. A maximum fall of 55 mm Hg (28%) in the systolic blood pressure and 25 mm Hg (29%) in the diastolic blood pressure occurred in one cat, and a fall of 45 mm Hg (24%) in the systolic blood pressure and 35 mm Hg (22%) in the diastolic blood pressure resulted in the other. These maximum falls in blood pressure occurred at 2–3 hours post-dose and the blood pressure had returned to pre-dose levels at 24 hours. Heart rate remained virtually unchanged throughout the study. The compound had no effect on pupil size or gastro-intestinal motility and caused no sedation at this dose level.

iii. Treatment of normotensive dogs and cats with 2 or 3 daily doses of 100 or 300 mg/kg p.o. of Example 3 produced no side effects such as sedation or diarrhoea in the conscious animal. In the anaesthetised animal, this pre-treatment had no effect on the blood pressure responses to noradrenaline and tyramine and did not reduce the contraction of the nictitating membrane to stimulation of the superior cervical nerve. In contrast 2 daily doses of reserpine 3 mg/kg p.o. produced sedation and diarrhoea, in the conscious animal, and affected responses to noradrenaline, tyramine and stimulation of the superior cervical nerve in the anaesthetised animal.

iv. When administered acutely to rodents, the compound of Example 2 was found to deplete heart but not brain monoamines and thus have an action similar to syrosingopine and methoserpidine (two reserpine analogues introduced to clinicians as compound which lower blood pressure but cause less sedation than reserpine). However, the compound of Example 2 was found to be a more potent antihypertensive than methoserpidine in hypertensive rats, and although equiactive with syrosingopine it differed from the latter in producing no observable side effects (sedation, ptosis, diarrhoea) when given repeatedly at a antihypertensive dose level (100 mg/kg p.o./day). In mice, the compound of Example 2 was markedly less toxic than syrosingopine, and in particular displayed no sedative activity. This lack of sedative effect in the compound of Example 2 represents a considerable technical advance over the known compounds.

EXAMPLE 5

2,2-Dimethyl-5-methoxy-4-[1-(2-naphthylmethyl)-1,2,5,6-tetrahydropyrid-4-yl]-7-n-pentylchroman 2,2-Dimethyl-5-methoxy-7-n-pentyl-4-(4-pyridyl)-2H-chromene (3.90g.) was hydrogenated for 4.5 hours at 20° C and 30 p.s.i. in ethanol (100 ml) in the presence of 5% palladium on charcoal (0.50g.). The solution was filtered and evaporated to dryness under reduced pressure to yield 2,2-dimethyl-5-methoxy-7-n-pentyl-4-(4-pyridyl) chroman as a yellow oil (3.90g.). (This compound was also prepared in low yield via treatment of 2,2-dimethyl-7-n-pentyl-4-(4-pyridyl) chroman-5-ol with 1) sodium hydride and 2) iodomethane in benzene).

This 4-(4-pyridyl)chroman (4.50g.), 2-bromomethylnaphthalene (2.98g.) and acetone (50 ml.) were refluxed for 8 hours. After cooling, diethyl-ether (900 ml.) was added and the resulting precipitate (6.50g.) was filtered. Recrystallisation from ethanol/diethylether yielded 4-(2,2-dimethyl-5-methoxy-7-n-pentyl-chroman-4-yl)-1-(2-naphthylmethyl) pyridinium bromide as pale yellow microcrystals (5.89g.) mp 177°–179° C.

This pyridinium bromide (5.86g.) was dissolved in a mixture of ethanol (70 ml.) and water (23 ml.) and sodium borohydride (0.74g.) was added portionwise to the stirred solution at ambient temperature. At the end of the addition, the solution was stirred for a further 0.5 hours and was then diluted with diethyl ether (300 ml.) and water (300 ml.). The organic layer was separated, dried over anhydrous potassium carbonate and evaporated under reduced pressure. The residual amber gum (4.96g.) was purified via column chromatography on silica gel using 60°–80° petroleum ether/ethyl acetate mixtures as eluent to give 2,2-Dimethyl-5-methoxy-4-[1-(2-naphthylmethyl)-1,2,5,6-tetrahydropyrid-4-yl]-7-n-pentylchroman as an orange oil (2.70g.).

EXAMPLE 6

Using procedures analogous to those described in Examples 1 and 2, the following compound is prepared 7-(2-Octyl)-2,2-dimethyl-4-[1-(2-naphthylmethyl-1,2,5,6-tetrahydro-4-pyridyl)-chroman-5-ol.

EXAMPLE 7

2,2-Dimethyl-5-(2-dimethylaminoethoxy)-4-[1-(2-naphthylmethyl)-1,2,5,6-tetrahydropyrid-4-yl]-7-n-pentylchroman dihydrochloride Sodium hydride (0.45g. of 80% dispersion in mineral oil, washed free of oil with 40°–60° petroleum ether immediately prior to use) was added cautiously in small portions to a stirred solution of 7-n-pentyl-4-[1-(2-naphthylmethyl)-1,2,5,6-tetrahydropyrid-4-yl]-2,2-dimethylchroman-5-ol monohydrate (4.87g., prepared as described in Examples 2 and 3) in dry toluene (60ml.). At the end of the addition, the solution was refluxed for 30 minutes, by which time frothing and the evolution of hydrogen had ceased. A solution of 2-dimethylaminoethyl chloride (1.18g.) in dry toluene (20 ml.) was then added dropwise to the refluxing mixture over 30 minutes. The mixture was then refluxed for a further 3 hours. After cooling, water (50 ml.) was added to the stirred mixture and the organic layer was separated, dried over anhydrous potassium carbonate, and evaporated to yield a straw-coloured oil.

This residual oil was dissolved in ethanol and treated with ethereal hydrogen chloride. The gum which separated was induced to solidify by trituration under dry ether. This crude product (4.17g.) was recrystallised from ethanol-ether to yield the desired 5-(2-dimethylaminoethoxy) chroman dihydrochloride as a dihydrate (3.34g.), mp 170°–179° C.

EXAMPLE 8

5-Acetoxy-2,2-dimethyl-4-[1-(2-naphthylmethyl)-1,2,5,6-tetrahydropyrid-4-yl]-7-n-pentylchroman.

A mixture of 7-n-pentyl-4-[1-(2-naphthylmethyl)-1,2,5,6-tetrahydropyrid-4-yl]-2,2-dimethylchroman-5-ol monohydrate (2.43g., prepared as described in Examples 2 and 3), anhydrous sodium acetate (0.43g.) and acetic anhydride (15.20 ml.) was refluxed for 4 hours. The mixture was then poured into ice-water (150ml.) with stirring and the solution was cautiously basified with sodium bicarbonate solution. The mixture was then extracted with ether and the ether extracts were dried over anhydrous potassium carbonate and evaporated to yield a straw-coloured gum (2.43g.). Purification via column-chromatography on silica gel using ethylacetate-60°–80° petroleum ether mixtures as eluent yielded the desired acetate as a colourless (1.63g.) which discoloured on standing.

EXAMPLE 9

4-Diethylaminobutoxy-2,2-dimethyl-4-[1,[(2-naphthylmethyl)-1,2,5,6-tetrahydropyrid-4-yl]-7-n-pentylchroman-5-yl dihydrochloride.

7-n-pentyl-4-[1-(2-naphthylmethyl)-1,2,5,6-tetrahydropyrid-4-yl]-2,2-dimethylchroman-5-ol monohydrate (4.57g., prepared as described in Examples 2 and 3), 4-diethylaminobutyric acid hydrochloride (1.96g.) and dicyclohexylcarbodiimide (2.10g.) were dissolved together in dry dichloromethane (150ml.) and the solution was stirred for 5 days at ambient temperature. The resulting precipitate of dicyclohexylurea was removed by filtration and the filtrate was evaporated to dryness in vacuo. The residual amorphous foam was dissolved in the minimum of ethanol and dry ether was added causing an off-white solid to be precipitated. This solid (2.90g.) was filtered off and the filtrate was treated with ethereal hydrogen chloride to give another off-white precipitate (2.86g.) which was collected by filtration,. These two solids were combined and recrystallised from ethanol-ether to yield the desired 4-diethylaminobutyrate dihydrochloride as hygroscopic, off-white microcrystals (3.79g.), mp 96° C upwards (vague).

What we claim is:

1. A pharmaceutical composition useful for treating hypertension in humans and animals which comprises an antihypertensively effective amount of a compound of the formula:

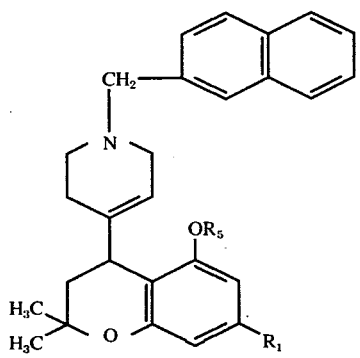

(I)

or a pharmaceutically acceptable non-toxic salt thereof, wherein $R_1$ is alkyl of 5 to 8 carbon atoms which is straight chained or $\alpha$-substituted by a methyl group or $\alpha,\alpha$-disubstituted by methyl groups and $R_5$ is hydrogen, $R_6$ or $CO.R_6$ wherein $R_6$ is alkyl of 1 to 4 carbon atoms or alkyl of 1 to 6 carbon atoms substituted by $NR_7R_8$ wherein $R_7$ and $R_8$ are each hydrogen or alkyl of 1 to 4 carbon atoms or $NR_7R_8$ is pyrrolidino, piperidino or morpholino, in combination with a pharmaceutically acceptable, non-toxic, inert diluent or carrier.

2. A composition according to claim 1 wherein $R_1$ is alkyl of 5 or 6 carbon atoms and $R_5$ is hydrogen.

3. A composition according to claim 1 wherein the compound is of the formula

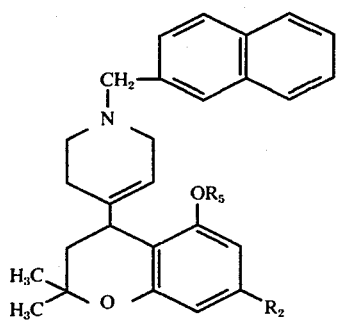

or a pharmaceutically acceptable non-toxic salt thereof wherein $R_2$ is n-amyl, n-hexyl or 2-hexyl and $R_5$ is hydrogen, $R_6$ or $CO.R_6$ wherein $R_6$ is alkyl of 1 to 4 carbon atoms.

4. A composition according to claim 3 wherein $R_2$ is n-amyl.

5. A composition according to claim 1 wherein the compound is of the formula

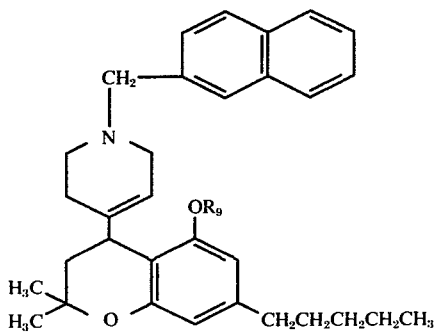

or a pharmaceutically acceptable non-toxic acid addition salt thereof wherein $R_9$ is hydrogen, methyl or acetyl.

6. A composition according to claim 1 wherein the compound is of the formula

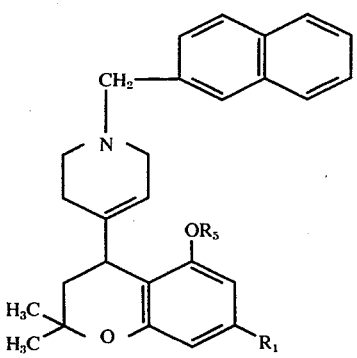

(I)

or a pharmaceutically acceptable non-toxic salt thereof wherein $R_1$ is alkyl of 5 to 8 carbon atoms which is straight chained or $\alpha$-substituted by a methyl group or $\alpha,\alpha$-disubstituted by methyl groups and $R_5$ is hydrogen, $R_6$ or $CO.R_6$ wherein $R_6$ is alkyl of 1 to 4 carbon atoms or alkyl of 1 to 4 carbon atoms substituted by $NR_7R_8$ wherein $R_7$ is hydrogen or alkyl of 1 to 4 carbon atoms, $R_8$ is hydrogen or alkyl of 1 to 4 carbon atoms or $NR_7R_8$ is pyrrolidino, piperidino or morpholino ring.

7. The composition according to claim 1 wherein the compound is 7-(2-Hexyl)-4-[1-(2-naphthylmethyl)-1,2,5,6-tetrahydro-4-pyridyl]-2,2-dimethylchroman-5-ol.

8. The composition according to claim 1 wherein the compound is 7-n-Pentyl-4-[1-(2-naphthylmethyl)-1,2,5,6-tetrahydro-4-pyridyl]-2,2-dimethylchroman-5-ol.

9. The composition according to claim 1 wherein the compound is 7-n-Pentyl-4-[1-(2-naphthylmethyl)-1,2,5,6-tetrahydro-4-pyridyl]-2,2-dimethylchroman-5-ol monohydrate.

10. The composition according to claim 1 wherein the compound is 2,2-Dimethyl-5-methoxy-4-[1-(2-naphthylmethyl)-1,2,5,6-tetrahydropyrid-4-yl]-7-n-pentylchroman.

11. The composition according to claim 1 wherein the compound is 7-(2-Octyl)-2,2-dimethyl-4-[1-(2-naphthylmethyl)-1,2,5,6-tetrahydro-4-pyridyl]chroman-5-ol.

12. The composition according to claim 1 wherein the compound is 5-acetoxy-2,2-dimethyl-4-[1-(2-naphthylmethyl)-1,2,5,6-tetrahydropyrid-4-yl]-7-n-pentyl-chroman.

13. The composition according to claim 1 wherein the compound is 2,2-dimethyl-5-(2-dimethylaminoethoxy)-4-[1-(2-naphthylmethyl)-1,2,5,6-tetrahydropyridyl-4-yl]-7-n-pentyl chroman dihydrochloride dihydrate.

14. The composition according to claim 1 wherein the compound is 4-diethylaminobutoxy-2,2-dimethyl-4-[1-(2-naphthylmethyl)-1,2,5,6-tetrahydropyrid-4-yl]-7-n-pentylchroman-5-yl [4-diethyl-aminobutyrate]-dihydrochloride.

15. A method of treating hypertension in humans and animals which comprises administering to a human or animal in need thereof an antihypertensively effective amount of a compound of the formula

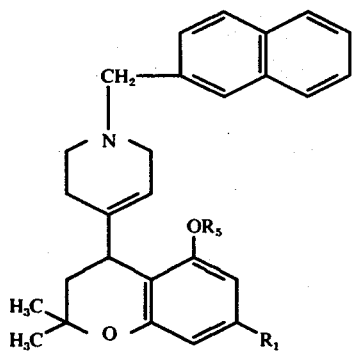

(I)

or a pharmaceutically acceptable non-toxic salt thereof, wherein $R_1$ is alkyl of 5 to 8 carbon atoms which is straight chained or α-substituted by a methyl group or α,α-disubstituted by methyl groups and $R_5$ is hydrogen, $R_6$ or $CO.R_6$ wherein $R_6$ is alkyl of 1 to 4 carbon atoms or alkyl of 1 to 6 carbon atoms substituted by $NR_7R_8$ wherein $R_7$ and $R_8$ are each hydrogen or alkyl of 1 to 4 carbon atoms or $NR_7R_8$ is a pyrrolidino, piperidino or morpholino.

16. A method according to claim 15 wherein $R_1$ is alkyl of 5 or 6 carbon atoms and $R_5$ is hydrogen.

17. A method according to claim 15 wherein the compound is of the formula

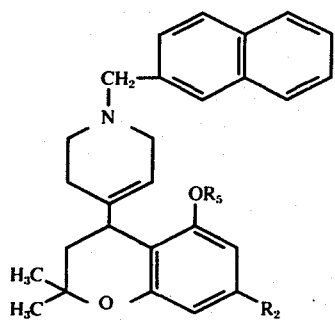

or a pharmaceutically acceptable non-toxic salt thereof wherein $R_2$ is n-amyl, n-hexyl or 2-hexyl and $R_5$ is hydrogen, $R_6$ or $CO.R_6$ wherein $R_6$ is alkyl of 1 to 4 carbon atoms.

18. A method according to claim 17 wherein $R_2$ is n-amyl.

19. A method according to claim 15 wherein the compound is of the formula

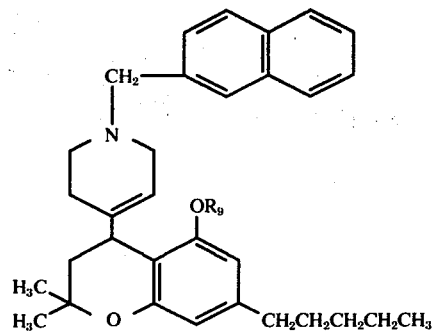

or a pharmaceutically acceptable non-toxic acid addition salt thereof wherein $R_9$ is hydrogen, methyl or acetyl.

20. A method according to claim 15 wherein the compound is of the formula

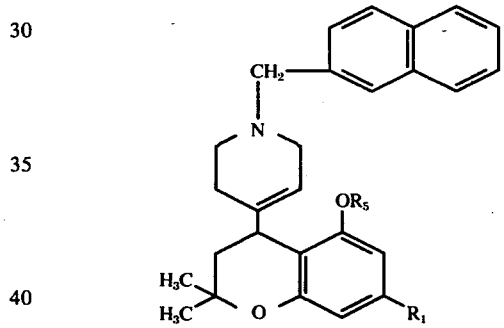

or a pharmaceutically acceptable non-toxic salt thereof wherein $R_1$ is alkyl of 5 to 8 carbon atoms which is straight chained or α-substituted by a methyl group or α,α-disubstituted by methyl groups and $R_5$ is hydrogen, $R_6$ or $CO.R_6$ wherein $R_6$ is alkyl of 1 to 4 carbon atoms or alkyl of 1 to 4 carbon atoms substituted by $NR_7R_8$ wherein $R_7$ is hydrogen or alkyl of 1 to 4 carbon atoms, $R_8$ is hydrogen or alkyl of 1 to 4 carbon atoms or $NR_7R_8$ is a pyrrolidino, piperidino or morpholino ring.

21. A method according to claim 15 wherein the compound is 7-(2-Hexyl)-4-[1-(2-naphthylmethyl)-1,2,5,6-tetrahydro-4-pyridyl]-2,2-dimethylchroman-5-ol.

22. A method according to claim 15 wherein the compound is 7-n-Pentyl-4-[1-(2-naphthylmethyl)-1,2,5,6-tetrahydro-4-pyridyl]-2,2-dimethyl-chroman-5-ol.

23. A method according to claim 5 wherein the compound is 7-n-Pentyl-4-[1-(2-naphthylmethyl)-1,2,5,6-tetrahydro-4-pyridyl]-2,2-dimethylchroman-5-ol monohydrate.

24. A method according to claim 15 wherein the compound is 2,2-Dimethyl-5-methoxy-4-[1-(2-naphthylmethyl)-1,2,5,6-tetrahydropyrid-4-yl]-7-n-pentyl-chroman.

25. A method according to claim 15 wherein the compound is 7-(2-Octyl)-2,2-dimethyl-4-[1(2-naphthylmethyl)-1,2,5,6-tetrahydro-4-pyridyl]-chroman-5-ol.

26. A method according to claim 15 wherein the compound is 5-acetoxy-2,2-dimethyl-4-[1-(2-naphthylmethyl)-1,2,5,6-tetrahydropyrid-4-yl]-7-n-pentylchroman.

27. A method according to claim 15 wherein the compound is 2,2-dimethyl-5-(2-dimethylaminoethoxy)-4-[1-(2-naphthylmethyl)-1,2,5,6-tetrahydropyridyl-4-yl]-7-n-pentyl chroman dihydrochloride dihydrate.

28. A method according to claim 15 wherein the compound is 4-diethylaminobutoxy-2,2-dimethyl-4-[1-(2-naphthylmethyl)-1,2,5,6-tetrahydropyrid-4-yl]-7-n-pentylchroman-5-yl dihydrochloride.

29. A composition according to claim 1 in oral administration form.

30. A composition according to claim 1 in parenteral administration form.

31. A method according to claim 17 wherein the administration is oral.

32. A method according to claim 17 wherein the administration is parenteral.

* * * * *